United States Patent
Lynam et al.

(10) Patent No.: US 7,946,505 B2
(45) Date of Patent: May 24, 2011

(54) ENVIRONMENTAL CONTROL SYSTEM FOR A VEHICLE

(75) Inventors: Niall R. Lynam, Holland, MI (US);
Patrick J. Lawlor, Clontarf (IE);
Garrett Coady, Palmerstown (IE)

(73) Assignee: Magna Donnelly Engineering GmbH, Sailauf (DE)

( * ) Notice: Subject to any disclaimer, the term of this patent is extended or adjusted under 35 U.S.C. 154(b) by 710 days.

(21) Appl. No.: 11/662,666

(22) PCT Filed: Sep. 15, 2005

(86) PCT No.: PCT/EP2005/010071
§ 371 (c)(1),
(2), (4) Date: Nov. 26, 2007

(87) PCT Pub. No.: WO2006/029901
PCT Pub. Date: Mar. 23, 2006

(65) Prior Publication Data
US 2008/0121034 A1 May 29, 2008

(30) Foreign Application Priority Data

Sep. 15, 2004 (IE) .................................. S2004/0614
Dec. 14, 2004 (IE) .................................. S2004/0838

(51) Int. Cl.
*F24F 3/14* (2006.01)
*F25B 49/00* (2006.01)
*G01N 25/02* (2006.01)
*G01K 3/00* (2006.01)
*B60H 1/00* (2006.01)

(52) U.S. Cl. ....... 236/44 C; 62/176.6; 374/28; 374/109; 165/202

(58) Field of Classification Search .................. 165/202, 165/204; 73/170.17, 335.04; 236/44 C; 62/176.6, 176.1; 340/425.5; 374/28, 109
See application file for complete search history.

(56) References Cited

U.S. PATENT DOCUMENTS 4,002,959 A 1/1977 Schadlich et al.
4,389,990 A 6/1983 Murray
(Continued)

FOREIGN PATENT DOCUMENTS

DE 19722577 A1 12/1998
(Continued)

OTHER PUBLICATIONS

International Search Report and Written Opinion of corresponding PCT Application No. PCT/EP2005/010071, filed Sep. 15, 2005.

*Primary Examiner* — Lisa M Caputo
*Assistant Examiner* — Jonathan Dunlap
(74) *Attorney, Agent, or Firm* — Van Dyke, Gardner, Linn & Burkhart, LLP

(57) ABSTRACT

An environmental control system for a vehicle, in particular for predicting internal misting of a vehicle windscreen, the system comprising a windscreen temperature sensor assembly 28, an ambient humidity sensor assembly 32 and a second temperature sensor assembly 30 for sensing the temperature of the humidity sensor assembly 32. The windscreen temperature sensor assembly 28 is mounted on an interior rearview mirror support bracket 10 for engagement with the interior surface 18 of the windscreen, and the second temperature and humidity sensor assemblies are mounted within a rearview mirror housing 12 mounted to the mirror support bracket 10.

17 Claims, 7 Drawing Sheets

U.S. PATENT DOCUMENTS

| | | | |
|---|---|---|---|
| 4,418,298 A | 11/1983 | Suzuki et al. | |
| 4,427,931 A | 1/1984 | Tsukihashi | |
| 4,481,448 A | 11/1984 | Bishop | |
| 4,511,829 A | 4/1985 | Wisniewski | |
| 4,523,134 A | 6/1985 | Kinoshita et al. | |
| 4,562,393 A | 12/1985 | Loyzim et al. | |
| 4,583,028 A | 4/1986 | Angersbach et al. | |
| 4,626,962 A | 12/1986 | Ahn et al. | |
| 4,665,350 A | 5/1987 | Angi et al. | |
| 4,749,922 A | 6/1988 | Hoppe et al. | |
| 4,803,410 A | 2/1989 | Shinohara et al. | |
| 4,893,067 A | 1/1990 | Bhagwat et al. | |
| 4,893,215 A | 1/1990 | Urushiwara et al. | |
| 4,899,256 A | 2/1990 | Sway-Tin | |
| 4,910,967 A * | 3/1990 | Takahashi | 165/233 |
| 4,999,556 A | 3/1991 | Masters | |
| 5,070,267 A | 12/1991 | Sano et al. | |
| 5,230,035 A | 7/1993 | Spring | |
| 5,285,146 A | 2/1994 | Pierret et al. | |
| 5,305,613 A * | 4/1994 | Hotta et al. | 62/230 |
| 5,329,238 A | 7/1994 | Hofsass et al. | |
| 5,363,024 A | 11/1994 | Hiratsuka et al. | |
| 5,521,785 A | 5/1996 | Schmidt et al. | |
| 5,594,307 A | 1/1997 | Adachi et al. | |
| 5,631,638 A * | 5/1997 | Kaspar et al. | 340/902 |
| 5,701,752 A * | 12/1997 | Tsunokawa et al. | 62/183 |
| 5,747,956 A | 5/1998 | Lamm | |
| 5,781,385 A | 7/1998 | Permuy | |
| 5,799,869 A | 9/1998 | Pichotta | |
| 5,917,296 A | 6/1999 | Frey et al. | |
| 5,988,517 A | 11/1999 | Bauer et al. | |
| 6,018,234 A | 1/2000 | de Savasse | |
| 6,049,069 A * | 4/2000 | Hochstein | 219/497 |
| 6,054,198 A | 4/2000 | Bunyan et al. | |
| 6,064,931 A | 5/2000 | Sawada et al. | |
| 6,112,807 A * | 9/2000 | Dage | 165/202 |
| 6,155,061 A * | 12/2000 | Davis et al. | 62/176.6 |
| 6,175,791 B1 | 1/2001 | Oouchi | |
| 6,180,880 B1 | 1/2001 | Loibl et al. | |
| 6,201,366 B1 | 3/2001 | Menegoli | |
| 6,281,827 B1 | 8/2001 | Hsieh | |
| 6,329,785 B1 | 12/2001 | Starkie et al. | |
| 6,386,742 B1 * | 5/2002 | DeLine et al. | 362/494 |
| 6,404,607 B1 | 6/2002 | Burgess et al. | |
| 6,422,062 B1 | 7/2002 | King et al. | |
| 6,428,172 B1 * | 8/2002 | Hutzel et al. | 359/838 |
| 6,508,408 B2 * | 1/2003 | Kelly et al. | 236/91 C |
| 6,587,338 B2 | 7/2003 | LaCroix et al. | |
| 6,668,917 B1 | 12/2003 | Zeng | |
| 6,809,530 B2 * | 10/2004 | Schmitt et al. | 324/689 |
| 6,843,424 B2 * | 1/2005 | Weber et al. | 236/49.3 |
| 6,862,893 B1 * | 3/2005 | Wang | 62/176.6 |
| 6,927,549 B2 | 8/2005 | Ashiya et al. | |
| 6,980,092 B2 * | 12/2005 | Turnbull et al. | 340/425.5 |
| 7,102,501 B2 * | 9/2006 | Lo Presti et al. | 340/501 |
| 7,197,927 B2 * | 4/2007 | Stauss et al. | 73/335.02 |
| 7,253,723 B2 * | 8/2007 | Lindahl et al. | 340/438 |
| 7,416,331 B2 * | 8/2008 | Ruttiger et al. | 374/142 |
| 7,446,427 B2 * | 11/2008 | Parker et al. | 307/10.1 |
| 2001/0018847 A1 * | 9/2001 | Lynam | 73/170.17 |
| 2002/0032510 A1 * | 3/2002 | Turnbull et al. | 701/49 |
| 2002/0053237 A1 * | 5/2002 | Lynam | 73/170.17 |
| 2002/0066281 A1 | 6/2002 | Gunasekera | |
| 2002/0150478 A1 | 10/2002 | Aoki | |
| 2003/0057899 A1 | 3/2003 | LaCroix | |
| 2003/0063900 A1 | 4/2003 | Wang et al. | |
| 2003/0086475 A1 * | 5/2003 | Schmitt et al. | 374/159 |
| 2003/0123224 A1 | 7/2003 | LaCroix et al. | |
| 2003/0126924 A1 * | 7/2003 | Lynam | 73/170.17 |
| 2003/0169522 A1 * | 9/2003 | Schofield et al. | 359/876 |
| 2003/0204292 A1 | 10/2003 | Wang et al. | |
| 2004/0032675 A1 * | 2/2004 | Weller et al. | 359/872 |
| 2004/0040321 A1 * | 3/2004 | Lo Presti et al. | 62/156 |
| 2004/0232773 A1 * | 11/2004 | Parker et al. | 307/10.1 |
| 2005/0028588 A1 * | 2/2005 | Mitter | 73/335.04 |
| 2007/0285789 A1 * | 12/2007 | Lindahl et al. | 359/604 |
| 2009/0295181 A1 * | 12/2009 | Lawlor et al. | 296/1.11 |

FOREIGN PATENT DOCUMENTS

| | | |
|---|---|---|
| EP | 1080955 A | 3/2001 |
| EP | 1564044 A | 8/2005 |

* cited by examiner

ENVIRONMENTAL CONTROL SYSTEM FOR A VEHICLE

The present application is a 371 U.S. national phase application of PCT Application No. PCT/EP2005/010071, filed Sep. 15, 2005, which claims priority on Irish patent application No. S2004/0614, filed Sep. 15, 2004, and Irish patent application No. S2004/0838, filed Dec. 14, 2004.

BACKGROUND OF THE INVENTION

1. Field of the Invention

This invention relates to an environmental control system for a vehicle, and in a preferred aspect to a system for predicting internal misting (fogging) of a vehicle window, especially but not limited to a vehicle windscreen.

2. Prior Art

U.S. Pat. No. 6,422,062 describes an integral sensor unit for predicting misting of a vehicle windscreen. The unit comprises a windscreen temperature sensor assembly, an ambient second temperature sensor assembly and an ambient air humidity sensor assembly, all contained within a common dome-shaped housing. In use the housing is attached to the interior surface of the windscreen and is connected via a multiconductor lead to a control unit located away from the housing, e.g. in the vehicle header.

A disadvantage of this unit is that its presence on the windscreen can be distracting to the driver and/or obscure his vision. Also, by placing the ambient air temperature and ambient humidity sensor assemblies in the same housing as the windscreen temperature sensor assembly they are necessarily enclosed near to the windscreen and hence may not be truly representative of the ambient temperature or atmosphere in the main passenger cabin of the vehicle. The presence of the unit and its cabling may also be aesthetically unattractive.

It is an object of the invention to provide an environmental control system for a vehicle, and especially but not limited to an improved system for predicting internal misting of a vehicle windscreen or other window which avoids or mitigates these disadvantages.

SUMMARY OF THE INVENTION

According to one aspect of the present invention there is provided a vehicle environmental control system comprising a window temperature sensor assembly for sensing the temperature of an interior surface of a vehicle window, a humidity sensor assembly for sensing the ambient air humidity within the vehicle, and a second temperature sensor assembly for sensing the temperature of the humidity sensor assembly, wherein the second temperature and humidity sensor assemblies are mounted within the vehicle away from the window temperature sensor assembly.

An advantage of the invention is that it provides design freedom to place the various sensor assemblies at positions most advantageous for a given situation, where the driver would not normally be aware of their presence. Hence they are not likely to distract the driver or obscure his vision. Further, by placing the second temperature and ambient humidity sensor assemblies away from the window temperature sensor assembly, which must necessarily be on or very close to the window, they are more likely to be representative of the ambient temperature or atmosphere in the main passenger cabin of the vehicle. Although in one application the outputs of the sensor assemblies are used in combination to predict internal window misting, their outputs can be used independently of each other, if desired, in order to measure the temperature and/or the humidity of the cabin, for the purposes of altering the environmental conditions of the cabin itself, in particular for the purposes of passenger comfort.

Preferably the window temperature sensor assembly is mounted for resilient biasing against the interior surface of the window.

In a preferred embodiment of the invention the system comprises a windscreen temperature sensor assembly for sensing the temperature of the interior surface of the windscreen, a humidity sensor assembly for sensing the ambient air humidity within the vehicle, and a second temperature sensor assembly for sensing the temperature of the humidity sensor assembly, wherein the windscreen temperature sensor assembly is mounted on an interior rearview mirror support bracket for engagement with the interior surface of the windscreen, and wherein the second temperature and humidity sensor assemblies are mounted within a rearview mirror housing mounted to the mirror support bracket.

In another aspect of the invention there is provided a temperature sensor assembly comprising a thermally insulating body, a temperature sensing element thermally insulated within the body, and a thermally conductive contacting element exposed externally of the body and in thermal communication with the temperature sensing element.

In yet another aspect of the invention there is provided a temperature sensor assembly comprising a thermally conductive element having a substantially planar exposed upper surface, a temperature sensing element in thermal communication with a lower surface of the thermally conductive element, a plurality of leads for the temperature sensing element extending downwardly away from said lower surface, and a generally tubular thermally insulating housing assembly having an upper end surrounding and supporting the temperature sensing element, the tubular housing assembly extending downwardly away from said lower surface of the thermally conductive element and having an internal air gap surrounding said leads.

In a still further aspect of the invention there is provided a mirror mounting system comprising a mounting bracket adapted for releasable connection to a vehicle window, and a sensor resiliently mounted to the bracket at a position such that, when the bracket is connected to the vehicle window, the sensor is urged against the window.

BRIEF DESCRIPTION OF THE DRAWINGS

Embodiments of various aspects of the invention will now be described, by way of example, with reference to the accompanying drawings, in which.

DETAILED DESCRIPTION OF A PREFERRED EMBODIMENT

Figure 1:
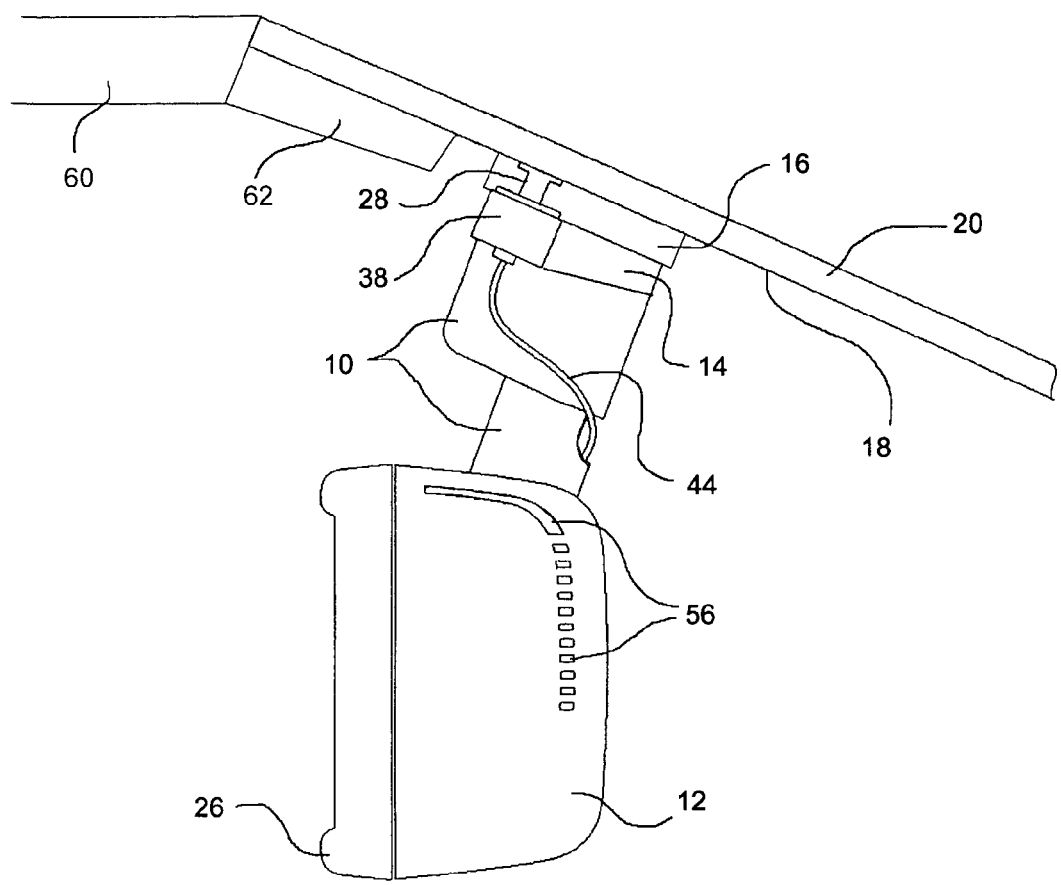
FIG. 1 is a side view of a vehicle interior rearview mirror assembly forming part of a vehicle environmental control system according to one aspect of the invention.

Referring now to the drawings, there is illustrated a vehicle environmental control system which comprises a mirror assembly comprising a mirror support bracket 10 and a rearview mirror housing 12. The bracket 10 has an upper end 14 for releasable attachment to a windscreen mounting member 16 which is adhesively secured to the interior surface 18 of the vehicle windscreen 20. The mounting member 16 may take the form of a windscreen button, rails, or any other suitable attachment element. The lower end of the bracket 10 is in the form of a ball 22, FIG. 3, which engages a complementary socket (not shown) within the mirror housing 12 to allow universal rotational adjustment of the mirror. The mirror housing 12 has a front opening 24 which is normally closed by a reflective element (also not shown) held in place by a bezel 26. The reflective element may comprise an electro-optic cell so that the reflectivity of the mirror can be varied according to prevailing conditions. The bracket 10 and mirror housing 12 are moulded from a rigid plastics material. The construction and operation of interior rearview mirror assemblies as just described are well-known to those skilled in the art and no further details are deemed necessary.

The environmental control system, of which the mirror assembly forms a part, is capable of performing a number of environmental control functions, in particular but not exclusively predicting internal misting of a vehicle window, for example a windscreen. The environmental control system comprises a windscreen temperature sensor assembly 28 for sensing the temperature of the interior surface of the windscreen, a second temperature sensor assembly 30, FIG. 5, in particular for sensing the temperature of a humidity sensor assembly 32, which humidity sensor assembly 32 is operable to sense the ambient air humidity within the vehicle. The windscreen temperature sensor assembly 28 is mounted on the bracket 10 for engagement with the interior surface of the windscreen, while both the second temperature sensor assembly 30 and humidity sensor assembly 32 are mounted on a printed circuit board (PCB) 34, FIGS. 4 and 5, within the mirror housing 12. The second temperature sensor assembly 30 is preferably mounted on, or is in direct contact with, the humidity sensor assembly 32, in order to be capable of sensing the temperature thereof, the reason for which is set out hereinafter. The second temperature sensor assembly is illustrated, in FIG. 5, as being separate from the The windscreen temperature sensor assembly 28 is a generally cylindrical body axially slidable within a hollow cylindrical sensor housing assembly 36, the latter being fitted into a hollow cylindrical moulding 38 integral with the upper end 14 of the bracket 10. A highly thermally conductive windscreen contacting element 42 is provided on the sensor assembly 28, which is preferably formed from a disc of metal or the like, for example aluminium, copper, brass, etc. The contacting element 42 is in thermal communication, preferably direct communication, with a temperature sensing element (not shown), preferably a thermistor, embedded within the 40, acting between annular flanges on the sensor assembly 28 and sensor housing temperature sensor assembly 28. A biasing means in the form of a compression spring assembly 36 respectively, resiliently biases the sensor assembly 28 at least partially out of the housing 36 into contact with the interior surface 18 of the windscreen 20.

An advantage of this arrangement is that a mounting system is provided, comprising the support bracket 10, which enables the sensor assembly 28 to be urged into contact with the windscreen 20 simultaneous with the attachment/securing of the mounting bracket 10 to the mounting member 16 on the windscreen 20. Thus no further operations are required in order to correctly position the sensor assembly 28 against the windscreen 20, thereby rendering the mounting system extremely beneficial in assembly line production of vehicles, allowing a "fit and forget" approach to be utilised. As the mirror assembly is attached to its windshield mounting button or other attachment member 16, the contacting element 42 of the sensor assembly 28 makes close and thermally intimate contact with the inner surface of the vehicle windshield.

The resilient mounting of the sensor assembly 28 performs two further important functions. The spring biasing of the sensor assembly 28 ensures that the sensor assembly 28 makes intimate and thermally conductive contact with the windscreen 20, in order to ensure that the sensor assembly 28, and in particular the contacting element 42, is thermally coupled with the windscreen 20, thus providing accurate readings from the sensor assembly 28 of the actual surface temperature at the inner surface of the vehicle windshield where dew/condensation may form. It is desirable that this surface temperature be what is measured and not the temperature of the air in the cabin adjacent the windshield (that may be at a higher temperature). In addition, the resilient mounting of the sensor assembly 28 allows for manufacturing tolerances, both in the mounting system itself and in the windscreen 20 against which the mounting assembly is to be seated via connection to the mounting member 16. It is well known that during the production of a product such as a vehicle or the like, having a large number of interrelated parts, manufacturing tolerances can accumulate, often resulting in a bad or inferior fit between various components. This can result in time being wasted, slowing down production and increasing the cost thereof. The resilient mounting of the temperature sensor assembly 28 allows for such variations in fit between the support bracket 10 and the windscreen 20. The temperature sensor assembly 28, and in particular the contacting element 42, prior to the mounting of the support bracket 10, projects from the moulding 38 a distance greater than is necessary to contact the windscreen 20. Thus when the support bracket 10 is mounted to the windscreen 20, the temperature sensor assembly 28 will be displaced inwardly against the action of the spring 40 in order to accommodate this negative dimensional difference. This will then ensure that the temperature sensor assembly 28 remains biased against the windscreen during use, so achieving and maintaining intimate thermal contact therewith.

From the foregone description it will be appreciated that the bracket 10 may be used with a sensor assembly other than the temperature sensor assembly 28, for example a rain sensor assembly (not shown) or the like, which must be seated against a vehicle window for the correct operation thereof.

Figure 2:
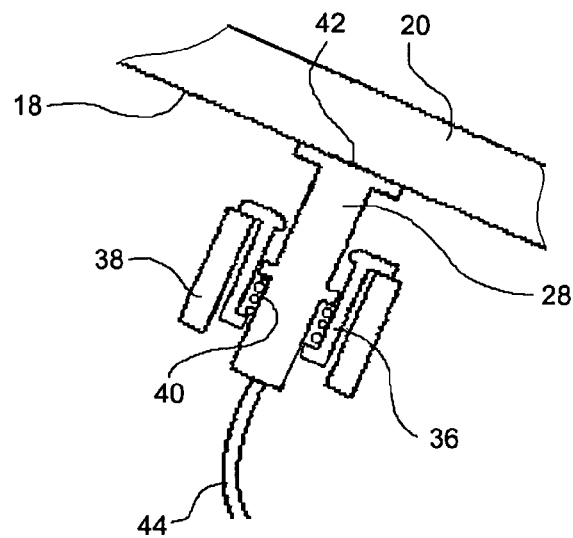
FIG. 2 is an enlarged cross-section of one embodiment of a windscreen temperature sensor assembly forming part of the vehicle environmental control system.
Figure 3:
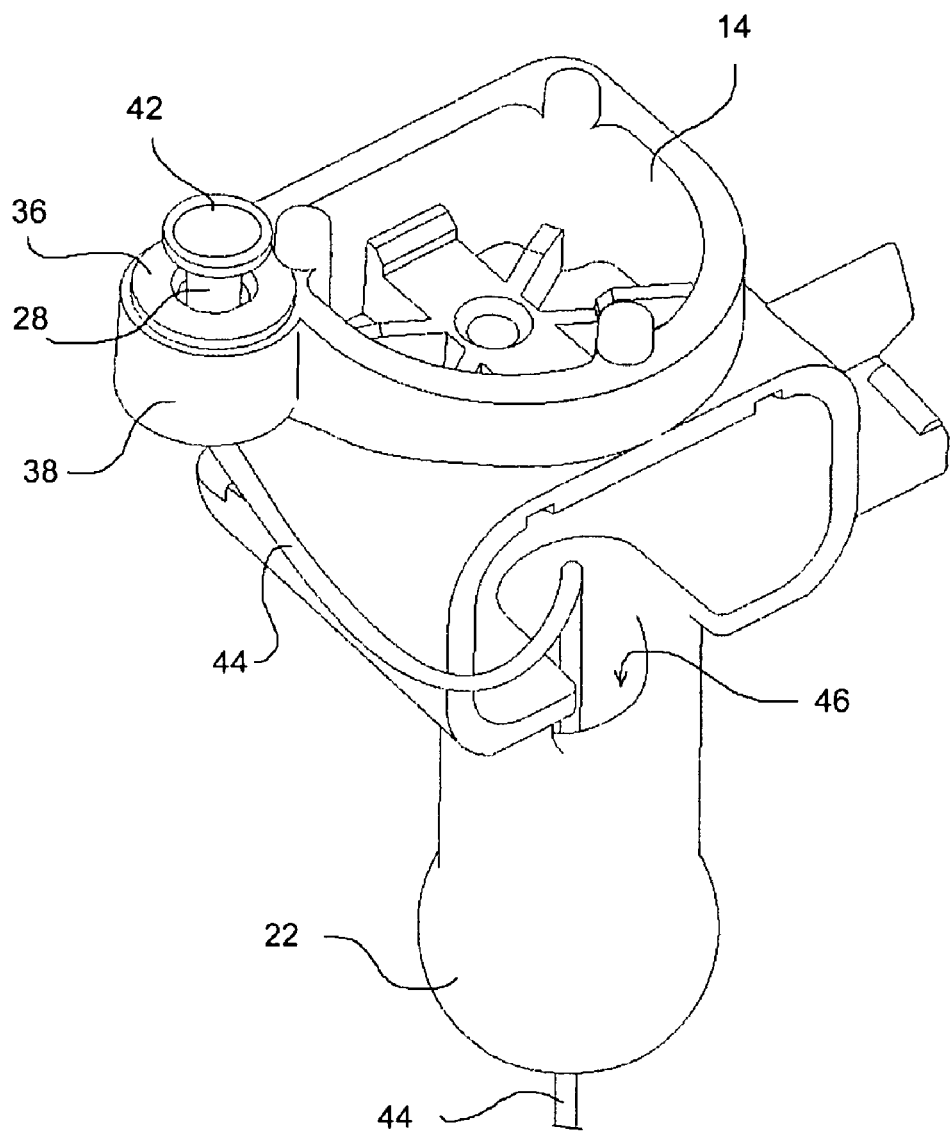
FIG. 3 is a top perspective view of a mirror support bracket assembly of FIG. 1, omitting a mirror housing.

Referring now in particular to FIGS. 2 and 3, and as mentioned above, the temperature sensor assembly 28 preferably contains a temperature sensing element in the form of a thermistor element connected to the PCB 34 by a cable 44. In this embodiment the cable 44 passes from the sensor assembly 28 to the PCB 34 via a central bore 46 in the bracket 10, FIG. 3. The bore 46 may also serve to allow electrical connection to other electronic equipment in the mirror housing 12, in a manner otherwise known to the automotive electrical connection art and thus will not be further described.

Figure 4:
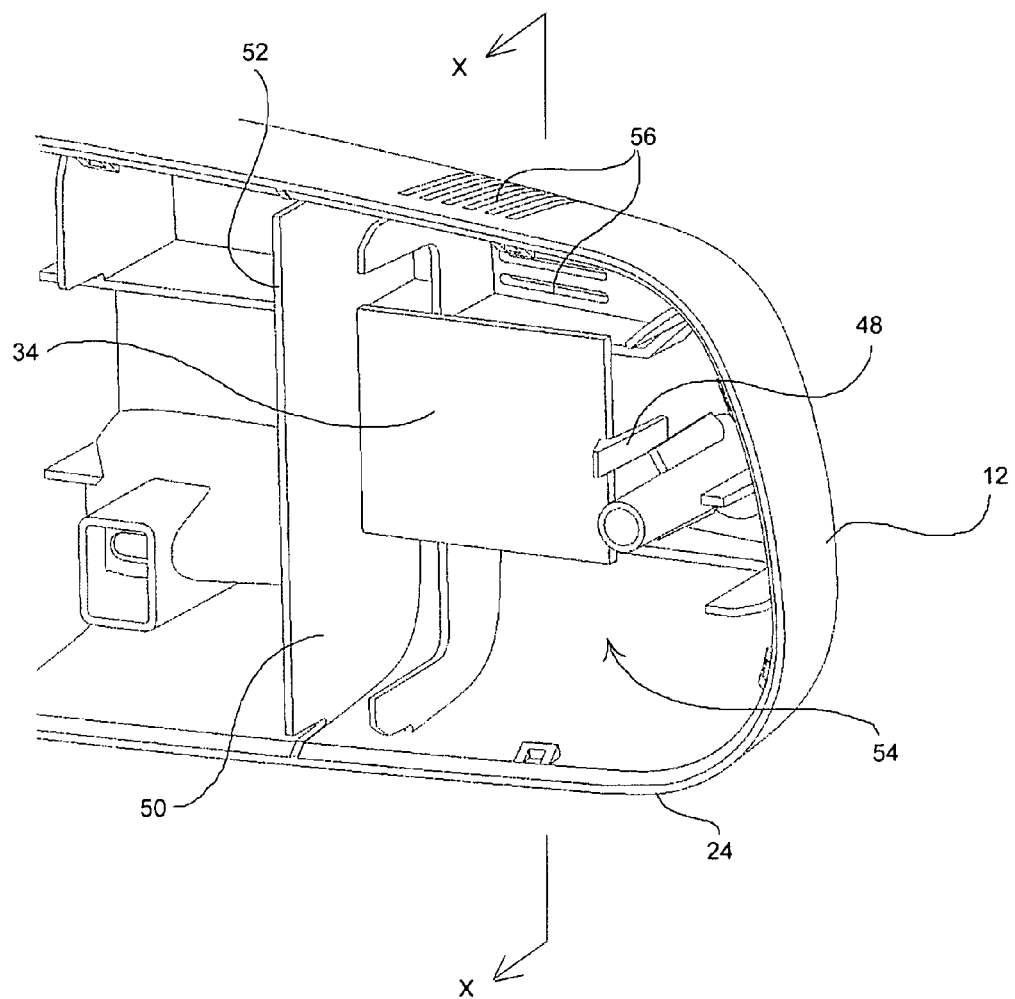
FIG. 4 is a view of the interior of part of the mirror housing of FIG. 1, omitting the reflective element.
Figures 5, 6:
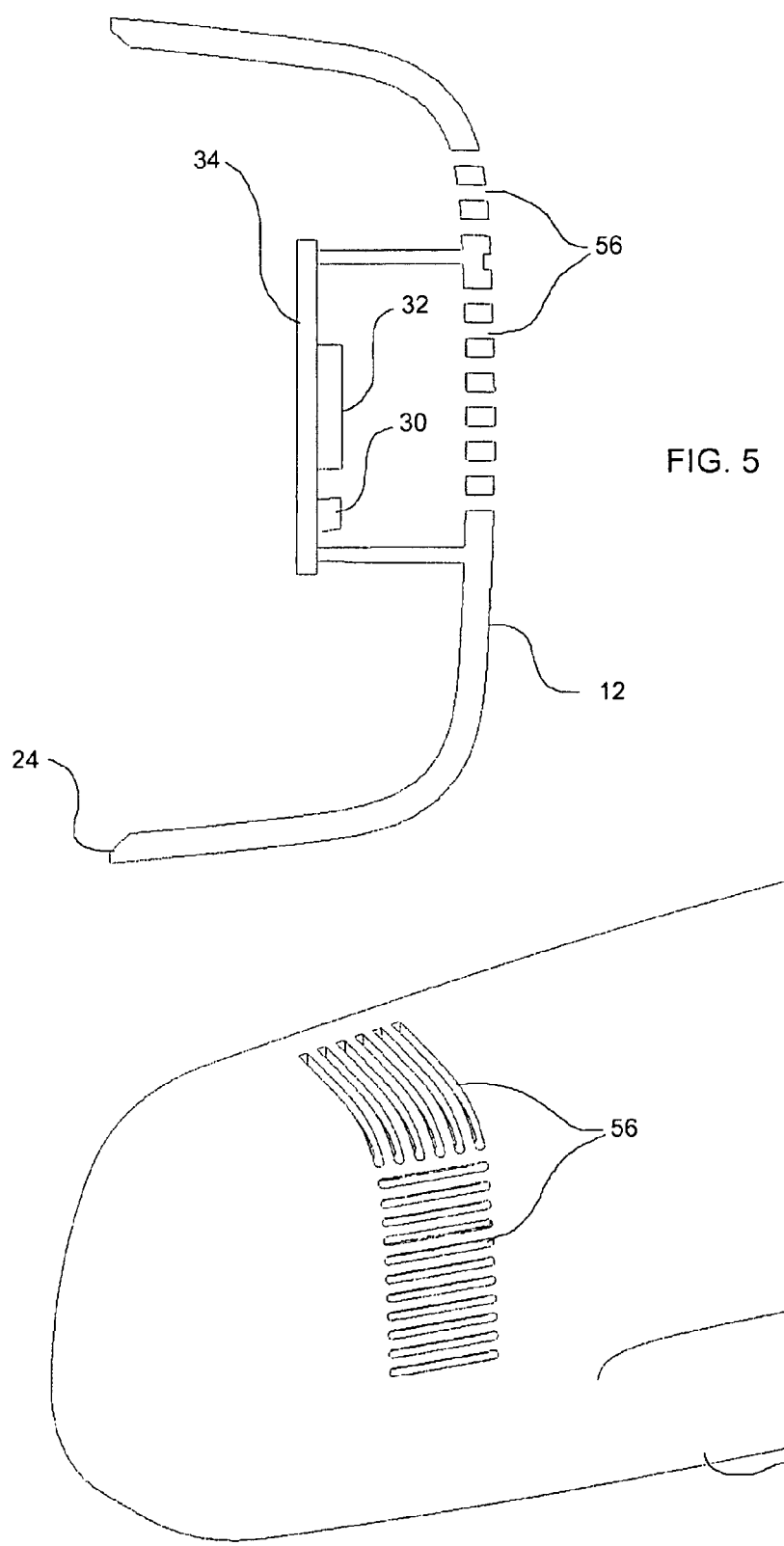
FIG. 5 is a cross-section on line X-X of FIG. 4.
FIG. 6 is an external view of the part of the mirror housing shown in FIG. 4.

The PCB 34 carrying the second temperature and humidity sensor assemblies 30, 32 is releasably mounted in the mirror housing 12 behind the reflective element. It is held in place by resilient clips 48 (only one is shown in FIG. 4) with the surface of the PCB 34 which carries the sensor assemblies 30, 32 facing the rear of the housing 12. An internal wall 50, whose front edge 52 abuts against the rear surface of the reflective element when fitted to the open front 24, defines within the mirror housing 12 a sub-compartment 54 containing the PCB 34. The PCB 34 is thus substantially thermally isolated in the sub-compartment 54, the wall 50 comprising a thermal barrier to heat generated by other electronic devices, if any, in the main body of the mirror housing. The cable 44 passes through a small hole (not shown) in the wall 50. Ventilation slots 56 in the rear of the housing, facing the surface of the PCB 34 carrying the second temperature and humidity sensor assemblies 30 and 32, allow ambient air to reach the sensor assemblies 30, 32 within the sub-compartment 54. The number of ventilation slots 56 is chosen such as to simulate, at least as closely as possible, the unobstructed flow of air past the second temperature and humidity sensor assemblies 30 and 32. In addition, as the natural flow of air within a vehicle cabin, in the region of the mirror housing 12, is upwardly along the interior surface of the windscreen 20, the ventilation slots 56 are preferably positioned on the rear of the mirror housing 12 to maximise the flow of air therethrough and onto the temperature and humidity sensor assemblies 30 and 32. If desired, a fan may be provided for actively supplying air to the second temperature and humidity sensor assemblies 30, 32.

The PCB 34, and in particular the component-bearing side thereof facing the ventilation slots 56, in addition to the second temperature sensor assembly 30 and humidity sensor assembly 32, are preferably coloured black, so as to be rendered invisible through the ventilation slots 56, in order to improve the aesthetics of the mirror housing 12.

In addition to the sensor assemblies 30 and 32 the PCB 34 also bears a controller (not shown) that includes a microprocessor that processes an algorithm including control logic which, in known manner, calculates the ambient dew point from the ambient air temperature and humidity as measured by the sensor assemblies 30 and 32. However, it will be appreciated that said microprocessor may be located remotely of the PCB 34, for example in separate control circuitry of the vehicle.

By mounting the second temperature sensor assembly 30 on or in direct contact with the humidity sensor assembly 32, the thermal mass of the humidity sensor assembly 32 will not give rise to a lag between the readings from the humidity sensor assembly 32 and the second temperature sensor assembly 30, in particular during periods of temperature and/or humidity fluctuation within the vehicle cabin. Thus it will be appreciated that the sensor assemblies 30, 32 could be located out of contact with one another, but the accuracy of any calculations based on their outputs may be negatively affected. If the sensor assemblies 30, 32 are to be separate from one another, then said separation should be kept to an absolute minimum.

If the ambient dew point is greater than (or is calculated/predicted to be imminently greater than) the temperature of the internal surface 18 of the windscreen 20, the control unit provides a signal indicating that the windscreen is likely to mist up or is actually misted up. In either case the control unit can communicate via the bore 46 with a vehicle heating, ventilation and air conditioning system so that the latter is controlled to change the ambient conditions in the vehicle passenger compartment to reduce or avoid such misting up. As an alternative or complimentary function, the control unit may be adapted to deploy other demisting and/or environmental control strategies.

One of the advantages of the system of the present invention is that it facilitates preemption of mist/fog build-up on the windshield surface so that the HVAC system of the vehicle can be actuated to prevent any misting occurring. This has an advantage over other known anti-fogging systems such as those based on optical detection of mist/fog build-up (such as via an optical sensor or a camera sensor) as these other systems typically operate to remove mist/fog as it is building up (or after it has built up). By contrast, the present embodiment is operable to prevent mist/fog from occurring.

Although the foregoing has described an embodiment in which the sensor assembly 28 is mounted on the mirror support bracket 10 for sensing the temperature of the interior surface of the windscreen 20, the sensor assembly 28 could alternatively by mounted in a suitable holder for sensing the temperature of the internal surface of any window of the vehicle, such as the rear window or a side window, in order to be able to predict misting of such window. Furthermore, the second temperature sensor assembly 30 and humidity sensor assembly 32 can be located elsewhere than in the mirror housing 12. For example, they could be mounted in the vehicle header 60, or in an electronics housing 62 located on the inside of the windscreen 20 between the vehicle header and the mirror support bracket 10. For example, the second temperature sensor assembly 30 and/or the humidity sensor assembly 32 can be included in a windshield electronics module such as are described in U.S. Pat. Nos. 6,824,281 and 6,690,268.

The outputs of the sensor assemblies 28, 30 and 32 may be used independently of one another by the controller to control other environmental aspects of the vehicle, such as internal humidity and air temperature.

Figure 7:
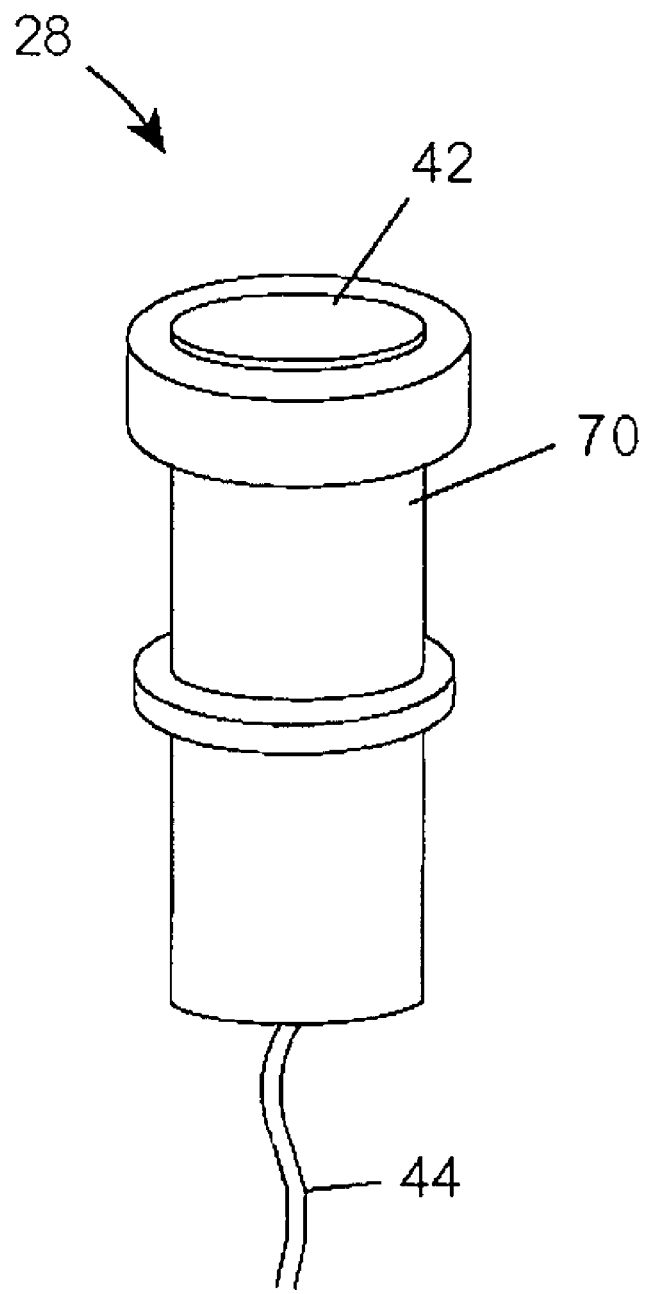
FIG. 7 is a perspective view of a temperature sensor assembly according to one aspect of the present invention.

Referring now to FIG. 7, there is illustrated an enlarged view of the temperature sensor assembly 28. The temperature sensor assembly 28 comprises a highly thermally conductive windscreen contacting element 42 which is preferably formed from a disc of metal such as aluminium, brass, copper, etc. The sensor assembly 28 further comprises a temperature sensing element in the form of a thermistor (not shown) embedded within a body 70 of highly thermally insulating material, preferably a polymeric material. The thermistor is in thermal contact, preferably direct contact, with the underside of the contacting element 42. In this way the contacting element 42 acts as a thermal coupling between the windscreen 20 and the thermistor within the body 70 such that the thermistor principally senses only the temperature at the windshield surface.

It will thus be appreciated that as the thermistor is embedded within the body 70, the contacting element 42 is the principal thermally conductive portion of the sensor assembly 28 which is exposed, and which in use will be urged against a vehicle window. It will therefore be appreciated that the temperature reading given by the temperature sensor assembly 28 will not be unduly affected by external factors such as the temperature of the air located directly adjacent the vehicle window, which in the absence of the thermally insulating body 70 could alter the temperature of the thermistor, and therefore the readings derived therefrom. The provision of the thermally insulating body 70 therefore improves the accuracy of the temperature sensor assembly 28. Although in use the temperature sensor assembly 28 will be spring biased against a vehicle window such as the windscreen 20, it is also envisaged that the contacting element 42 could itself be spring biased within the body 70, in order to further ensure an intimate thermally conductive contact between the contacting element 42 and the windscreen 20.

The temperature sensor assembly 28 further comprises a cable 44 in electrical connection with the thermistor, for electrically connecting the temperature sensor assembly 28 to any suitable circuitry (not shown), for example the PCB 34. As the cable 44 contacts the thermistor, the possibility exists for the cable 44 to act as a thermal sink. This could result in heat/cold being transferred to the thermistor, altering the temperature of the thermistor, and so distorting the readings derived therefrom. Thus to further improve the accuracy of measurement of the inner surface temperature of the windshield by the temperature sensor assembly 28, the cable 44 is preferably jacketed by thermally insulating material, or alternatively is formed from a conventional electrical conductor provided with a thermally insulating coating or the like (not shown) but with care being taken to minimize thermal transfer at the point that the electrical conductors within the cable make contact with the thermistor. This ensures that heat transfer cannot occur back along the cable 44.

Figure 8:
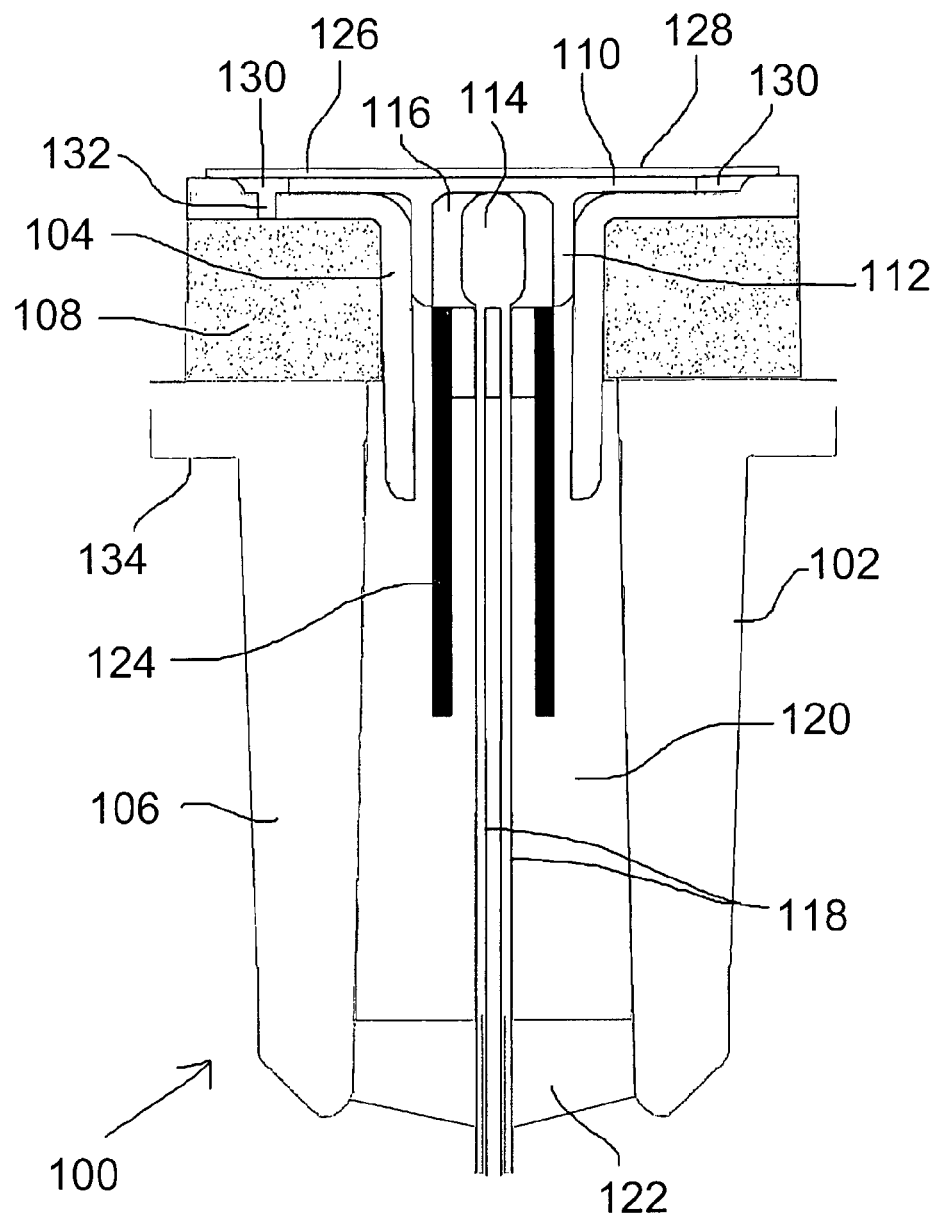
FIG. 8 is a cross-section of a temperature sensor assembly according to a further aspect of the invention.

FIG. 8 is a cross-section of a substantially circularly symmetric temperature sensor assembly 100 according to a further embodiment of the invention, which may be used in place of the sensor assembly 28 previously described and which we have found to provide a more accurate measurement of temperature than the previous sensor. In the following description of FIG. 8, and in the related claims, terms of orientation and direction such as "upper", "lower", "downwardly" and the like refer to the orientation of the sensor assembly as seen in FIG. 8 and do not limit its orientation in use.

The sensor assembly 100 comprises a generally tubular housing assembly 102 comprising, in this embodiment, three parts—an upper part 104, a lower part 106 and an intermediate part 108 interposed between the upper and lower parts. The upper and lower parts 104, 106 have the cross-sectional shapes shown and are moulded from a thermally insulating plastics material, while the intermediate part 108 comprises a thermally insulating resiliently deformable material, in particular a foam annulus.

The bottom surface of a substantially flat circular copper plate 110 is supported by and is adhered to the top surface of the upper housing part 104, the bottom surface of the plate 110 having at its centre an integral tubular copper housing 112 which extends downwardly concentrically within the upper housing part 104. A temperature sensing element in the form of a thermistor 114 is secured within the copper housing 112 by a thermally conductive potting compound 116, the thermistor 114 being in intimate contact with the lower surface of the copper plate 110.

Thermistor leads 118 extend downwardly through the lower housing part 106, the latter having an internal air gap 120 surrounding the leads. A plug 122 of thermally insulating material is preferably but not essentially provided, in order to close the lower end of the housing part 106, the leads then passing through the plug 122. The upper ends of the leads 118, where they emerge from the thermistor 114, are protected by a tubular shroud 124 which forms part of the thermistor as a commercially available product.

A thermally conductive polymer layer 126 covers the copper plate 110, the upper substantially flat surface of the plate 110 making intimate large-area contact with the lower surface of the layer 126. The upper surface 128 of the layer 126 is substantially planar, but has sufficient flexibility or compliance to conform closely to the inside surface of a windscreen or other window against which the sensor assembly 100 is biased. The provision of the resiliently deformable intermediate part 108 also enables the various components supported thereby, in particular the thermistor 114, the copper plate 110, and the polymer layer 126, to be urged against a vehicle windscreen in similar fashion to the action provided by the spring 40 used with the windscreen temperature sensor assembly 28.

The polymer layer 126 extends onto the periphery of the upper housing part 104, thereby covering a lateral air gap 130 between the outside periphery of the metal plate 110 and the upper housing part 104. A small bleed hole 132 provides an escape path for air which might otherwise become trapped between the polymer layer 126 and plate 110 when the former is applied to the latter during manufacture.

In use the sensor assembly 100 may be mounted on a mirror support bracket, such as the bracket 10 (FIGS. 1 to 3), and in particular in a moulding similar to the moulding 38. The resiliently deformable intermediate part 108 therefore serves a dual purpose, both thermally insulating the thermistor 114 and ensuring that the polymer layer 126 is spring biased against the windscreen. Thus, as in the case of the embodiment of FIGS. 1 to 3, the sensor assembly 100, and in particular the upper surface 128 of the polymer layer 126, is automatically urged into, and maintained in, intimate contact with the inside surface of the windscreen when the bracket 10 is mounted on its windscreen mounting member 16.

In order to further thermally insulate the thermister 114, contact between the tubular housing assembly 102 and the bracket 10, in particular the moulding 38, is preferably kept to a minimum in order to reduce possible thermal leak between the bracket 10 and the sensor assembly 100. Thus, for example, a number of radially extending fins (not shown) or the like may be provided on the underside of the flange 134, in order to reduce the physical contact area between the flange 134 and the moulding 38, and thus reduce possible thermal leak therebetween. For stability, it is preferable to provide at least three such fins, spaced approximately 120° from one another. While more than three fins could be employed, this would increase the overall contact area between the flange 134 and the moulding 38. Similarly, a number of longitudinally extending fins (not shown) are preferably provided on the exterior of the lower housing part 106, again to act as a thermal buffer between the sensor assembly 100 and the moulding 38, while securing the sensor assembly 100 centrally within the moulding 38. Again the preferred number of longitudinally extending fins is three.

The advantage of this design is that the thermistor 114 is substantially thermally isolated from the environment by the three-part tubular housing assembly 102 and by the static air trapped in the air gaps 120 and 130. Thus the output of the thermistor 114 will more accurately reflect the temperature of the windscreen, or other surface against which the polymer layer 126 is pressed, due to the high conductivity of the copper plate 110 and thinness of the polymer layer 126. Further, the use of the polymer layer 126 lends itself better to the problem of sliding the sensor assembly 100 across the windscreen during the mounting of the bracket 10. It will be noted that in use the exposed part of the sensor assembly 100, being primarily the portion above the flange 134, is relatively short and broad, thereby avoiding unnecessary thermal exposure and reducing the possibility of inadvertent damage during mounting which might occur with a tall sensor assembly.

It should also be appreciated that the polymer layer 126 could be applied to the windscreen temperature sensor assembly 28 in order to improve the performance thereof. The polymer layer 126 could be applied directly onto the contacting element 42, or could be provided as a substitute for same.

Preferably the entire sensor assembly 100 has a low thermal mass, in order to avoid unduly affecting the temperature reading as might occur if the assembly 100 absorbed substantial heat from the windscreen.

It will be appreciated that as the second temperature sensor assembly 30 and the humidity sensor assembly 32, in particular the second temperature sensor assembly 30, are mounted away from the windscreen 20, they are capable of measuring the temperature and humidity respectively of the cabin of a vehicle, as opposed to the air located directly adjacent the windscreen 20 thereof. Thus the outputs of the second temperature sensor assembly 30 and the humidity sensor assembly 32 may be used other than in combination with the output of the temperature sensor assembly 28 or 100, in order to measure and consequently vary the temperature and/or humidity of the cabin, for reasons other than the possibility of misting of the vehicle windscreen 20, in particular for passenger comfort. The positioning of the sensor assemblies 30 and 32 within the mirror housing 12 is thus beneficial, as the sensor assemblies 30 and 32 are thus located close to a drivers upper body and head area, which are generally the most sensitive areas to environmental conditions.

Figure 9:
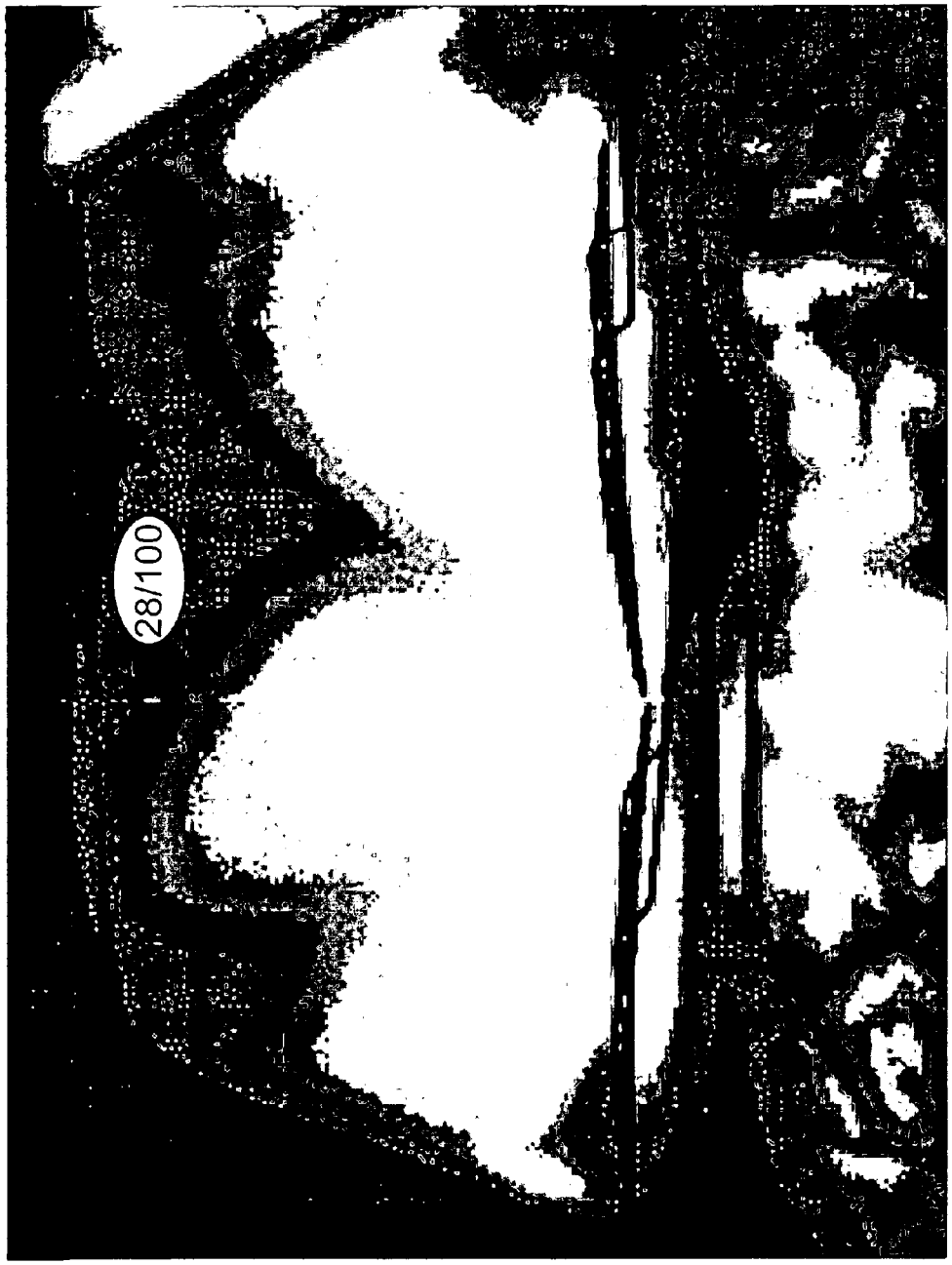
FIG. 9 shows the typical temperature distribution of a vehicle windscreen and preferred location of the temperature sensor.

FIG. 9 shows the typical temperature distribution of a vehicle windscreen. In FIG. 9 the lightest areas are the hottest, and it will therefore be seen that the upper 30 windscreen area is furthest from heat sources such as air-conditioning/heating outlets and this upper windshield area is the position where mist on the windshield will be last located during the demisting process. The upper windshield area also corresponds to a driver's line of sight. Thus, the upper windshield area is the preferred location of the temperature sensor assembly 28 or 100.

The invention claimed is:

1. A vehicle environmental control system comprising:
   an interior rearview mirror assembly comprising a mirror support bracket and a mirror head, wherein the mirror support bracket has a mounting portion for releasable attachment to a mounting button adhesively attached to an interior surface of a vehicle windshield, and wherein the mirror head includes a pivot element that pivotally attaches to a pivot element of the mirror support bracket to pivotally attach the mirror head to the mirror support bracket at the windshield of the vehicle;
   a window temperature sensor assembly for sensing the temperature of the interior surface of the vehicle windshield, wherein the window temperature sensor assembly is included in the mirror support bracket of the interior rearview mirror assembly and wherein, when the mounting portion of the mirror support bracket mounts to the mounting button attached at the interior surface of the vehicle windshield, a temperature sensing surface of the window temperature sensor assembly is biased toward and into contact with the interior surface of the vehicle windshield so as to enhance maintaining thermal contact therewith;
   a humidity sensor assembly for sensing the ambient air humidity within the passenger cabin of the vehicle and a second temperature sensor assembly for sensing ambient temperature within the passenger cabin of the vehicle, wherein the humidity sensor assembly and the second temperature sensor assembly are disposed at a location within the passenger cabin of the vehicle external and distant from the mirror support bracket;
   a controller including a microprocessor and control logic operable to calculate an ambient dew point from the ambient air temperature and humidity as sensed by the second temperature sensor assembly and the humidity sensor assembly; and
   wherein, when the calculated ambient dew point is greater than the temperature at the interior surface of the windshield as sensed by the window temperature sensor assembly, a vehicle climate control system, responsive to the controller, is controlled to change the ambient air conditions in the vehicle passenger compartment.

2. A system as claimed in claim 1, wherein the second temperature sensor assembly and the humidity sensor assembly are mounted adjacent an upper portion of the windshield.

3. A system as claimed in claim 1, wherein the second temperature sensor assembly and the humidity sensor assembly are mounted within the mirror head of the interior rearview mirror assembly.

4. A system as claimed in claim 3, wherein the second temperature sensor assembly and the humidity sensor assembly are mounted on a circuit board within the mirror head, and the window temperature sensor assembly is connected to the circuit board by a cable.

5. A system as claimed in claim 4, wherein the cable passes through a bore in the mirror support bracket of the interior rearview mirror assembly.

6. A system as claimed in claim 3, wherein the mirror head has ventilation openings to allow ambient air to reach the second temperature sensor assembly and the humidity sensor assembly within the mirror head.

7. A system as claimed in claim 6 wherein the ventilation openings are located in the rear of the mirror head.

8. A system as claimed in claim 6, wherein the number of ventilation openings is sufficient to simulate the unobstructed flow of air past the second temperature sensor assembly and the humidity sensor assembly.

9. A system as claimed in claim 6, wherein aspiration means are provided for actively supplying air to the second temperature sensor assembly and the humidity sensor assembly.

10. A system as claimed in claim 9 wherein the aspiration means comprises a fan.

11. A system as claimed in claim 3, wherein the mirror head has at least one internal wall defining a sub-compartment within the mirror head containing the second temperature sensor assembly and the humidity sensor assembly.

12. A system as claimed in claim 1, wherein the second temperature sensor assembly and the humidity sensor assembly are mounted within a vehicle header.

13. A system as claimed in claim 1, wherein the second temperature sensor assembly and the humidity sensor assembly are mounted within an electronics housing located between a vehicle header and the interior rearview mirror support bracket.

14. A system as claimed in claim 1, wherein the window temperature sensor assembly is maintained in direct engagement with the interior surface of the windshield.

15. A system as claimed in claim 1, wherein the window temperature sensor assembly is mounted for resilient biasing against the interior surface of the windshield.

16. A system as claimed in claim 1, wherein the output of the second temperature sensor assembly may be used for environmental control independently of the window temperature sensor assembly and the humidity sensor assembly.

17. A system for predicting internal misting of a vehicle windscreen, the system comprising:
   a windscreen temperature sensor assembly for sensing the temperature of the interior surface of the windscreen, wherein the windscreen temperature sensor assembly is included in an interior rearview mirror assembly and wherein, when the interior rearview mirror assembly mounts to a mounting button attached at the interior surface of the vehicle windscreen, a temperature sensing surface of the windscreen temperature sensor assembly is biased toward and into contact with the interior surface of the windscreen so as to enhance maintaining thermal contact therewith;

wherein the windscreen temperature sensor assembly is mounted on an interior rearview mirror support bracket for engagement with the interior surface of the windscreen when the interior rearview mirror support bracket mounts to the mounting button;

a humidity sensor assembly for sensing the ambient air humidity within the passenger cabin of the vehicle, and a second temperature sensor assembly for sensing the ambient air temperature within the passenger cabin of the vehicle, wherein the second temperature sensor assembly and the humidity sensor assembly are mounted within a rearview mirror housing mounted to the mirror support bracket;

a controller including a microprocessor and control logic that is operable to calculate an ambient dew point from the ambient air temperature and humidity as sensed by the second temperature sensor assembly and the humidity sensor assembly; and wherein, when the calculated ambient dew point is greater than the temperature at the interior surface of the windshield as sensed by the window temperature sensor assembly, a vehicle climate control system, responsive to the controller, is controlled to change the ambient air conditions in the vehicle passenger compartment.

* * * * *

UNITED STATES PATENT AND TRADEMARK OFFICE
CERTIFICATE OF CORRECTION

PATENT NO.         : 7,946,505 B2
APPLICATION NO.    : 11/662666
DATED              : May 24, 2011
INVENTOR(S)        : Niall R. Lynam, Patrick J. Lawlor and Garrett Coady It is certified that error appears in the above-identified patent and that said Letters Patent is hereby corrected as shown below:

Column 3
Line 50, Insert --humidity sensor assembly 32, for the purposes of clarity.-- after "the"
Line 61, Insert --temperature sensor assembly 28. A biasing means in the form of a compression spring-- after "the"
Line 63, Delete "temperature sensor assembly 28. A biasing means in the form of a compression spring" after "housing"

Column 9
Line 21, Delete "30" after "upper"

Signed and Sealed this
Twenty-ninth Day of May, 2012

David J. Kappos
*Director of the United States Patent and Trademark Office*